United States Patent
Lastow

(10) Patent No.: US 8,393,322 B2
(45) Date of Patent: Mar. 12, 2013

(54) INHALER COMPRISING A BASE HAVING A PLURALITY OF MEDICAMENT CONTAINING SEALED CAVITIES

(75) Inventor: Orest Lastow, Lund (SE)

(73) Assignee: AstraZeneca AB (SE)

(*) Notice: Subject to any disclaimer, the term of this patent is extended or adjusted under 35 U.S.C. 154(b) by 281 days.

(21) Appl. No.: 12/867,423

(22) PCT Filed: Feb. 11, 2009

(86) PCT No.: PCT/SE2009/050148
§ 371 (c)(1),
(2), (4) Date: Aug. 12, 2010

(87) PCT Pub. No.: WO2009/102276
PCT Pub. Date: Aug. 20, 2009

(65) Prior Publication Data
US 2010/0326440 A1    Dec. 30, 2010

Related U.S. Application Data

(60) Provisional application No. 61/027,865, filed on Feb. 12, 2008, provisional application No. 61/090,255, filed on Aug. 20, 2008.

(51) Int. Cl.
*A61M 15/00* (2006.01)
(52) U.S. Cl. ......... 128/203.21; 128/200.24; 128/203.15; 128/203.19
(58) Field of Classification Search ............. 128/200.24, 128/203.15, 203.19, 203.21
See application file for complete search history.

(56) References Cited

U.S. PATENT DOCUMENTS

2002/0134382 A1* 9/2002 Snow ................. 128/203.15
2007/0267016 A1* 11/2007 Thoemmes et al. ..... 128/203.12

FOREIGN PATENT DOCUMENTS

| EP | 1844806 | 10/2007 |
|---|---|---|
| GB | 2401548 | 11/2004 |
| WO | WO00/53248 | 9/2000 |
| WO | WO03/103563 | 12/2003 |
| WO | WO2005/030305 | 4/2005 |
| WO | WO 2006000758 | 1/2006 |

OTHER PUBLICATIONS

International Search Report issued on Jun. 8, 2009, in International Application No. PCT/SE2009/050148 (4 pages).

* cited by examiner

Primary Examiner — Melanie Hand
Assistant Examiner — Andrew S Lo
(74) *Attorney, Agent, or Firm* — Finnegan, Henderson, Farabow, Garrett, & Dunner, LLP

(57) ABSTRACT

An inhaler which comprises a base having a plurality of consecutive sealed cavities containing medicament. Foil portions are on one side attached to the base for sealing the medicament within respective associated cavities. A plurality of separating elements are attached to the other side of the foil portions, each separating element being associated with a respective cavity for separating a foil portion from that cavity. Each separating element can be moved-away from its associated cavity so that the sealing foil portion is separated from the cavity which is thereby uncovered so that medicament contained therein is enabled to become entrained in a fluid flow, and then returned with the attached foil portion to cover its associated cavity. A method of operating an inhaler is also disclosed.

13 Claims, 8 Drawing Sheets

INHALER COMPRISING A BASE HAVING A PLURALITY OF MEDICAMENT CONTAINING SEALED CAVITIES

This is a U.S. National Phase application of PCT/SE2009/050148, filed on Feb. 11, 2009, which claims the benefit of priority to U.S. Provisional Application No. 61/027,865, filed on Feb. 12, 2008, and U.S. Provisional Application No. 61/090,255, filed on Aug. 20, 2008, all of which are incorporated herein by reference in their entireties.

TECHNICAL FIELD

The present invention relates to an inhaler comprising a base having at least one cavity containing medicament, such as in the form of dry powder medicament. The present invention also relates to a method in connection with such an inhaler.

BACKGROUND OF THE INVENTION

There are different types of inhalers on the market. A pressurized Metered Dose Inhaler (pMDI) releases a fixed dose of substance in aerosol form. A powder inhaler generally releases a dose of powdered substance entrained in an air stream. In a powder inhaler the powder may be provided in a bulk container of the inhaler from which doses of powder are metered for dispensing. As an alternative to a bulk container, powder inhalers may comprise a single compartment or a plurality of compartments for containing discrete is doses of powdered substance. Such compartments may take the form of sealed blisters in a blister pack, a cavities-containing strip joined to a sealing strip or other suitable forms.

There are different solutions to opening compartments containing discrete doses of powder. WO 01/72605 discloses different embodiments of a dose strip for use with a powder inhaler. Various opening mechanisms are disclosed. For instance, in FIG. 4 a lid strip covers spaced apart blisters. Lid tabs are attached to the lid strip over each blister. A peel strip is joined to each lid tab. Pulling of the peel strip opens the blisters. In FIG. 22 of WO 01/72605 a dose strip comprises a number of blisters containing pharmaceutical powder. Each blister is connected to a respective plunger. A blister is opened by a slider having a wedge that engages a slot on the plunger. The wedge pulls the plunger down, breaking the seal and releasing pharmaceutical powder into a flow path, for inhalation.

SUMMARY OF THE INVENTION

An object of the present invention is to provide an alternative manner of handling sealed compartments or cavities and elements associated thereto inside an inhaler.

This and other objects, which will become apparent in the following disclosure, are accomplished by the invention defined in the accompanied claims.

The present invention is based on the insight that an opening element may be provided with dual functionality. Thus, after or before it has been used for opening a sealed compartment containing powder, it may have another function different from the opening function. In particular it has been realised that an opening element may be in the form of a flow path-defining element for guiding a fluid flow. It has also been realised that an opening element may subsequently function as a closing element for preventing possible powder remains to exit from a used compartment.

According to at least a first aspect of the invention, an inhaler is provided. The inhaler comprises a base having a plurality of medicament-containing sealed cavities which are consecutively movable to a dispensing position of the inhaler, foil portions which on one side are attached to the base for sealing the medicament is within respective associated cavities and which on an opposite side are attached to a plurality of separating elements, each separating element being associated with a respective cavity for separating a foil portion from that cavity, an actuator adapted to provide an impact on the separating element associated with the cavity currently located in the dispensing position, thereby moving that separating element to a removed position in which the separating element is moved-away from the cavity so that the sealing foil portion is separated from the cavity which is thereby uncovered so that medicament contained therein is enabled to become entrained in a fluid flow, wherein, in the removed position of the separating element, the attached foil portion at least partly defines a flow path for the medicament entrained from the cavity.

Thus, the separating element is not just discarded when it has been used to open the sealed cavity. Rather it now functions as a flow path-defining element together with the attached foil portion.

According to at least one example embodiment, the separating element comprises a returned position in which the separating element with the attached foil portion is moved back to cover its associated cavity. Thus, the separating element is not just discarded after it has caused the foil to separate from the cavity, but may be returned to cover that cavity after a fluid flow has entrained powder therefrom. This will make it difficult for any remaining powder to exit the covered used cavity, thus reducing the risk of dose variation which could occur if such remaining powder would be entrained in a following inhalation. It also reduces the risk of remaining powder exiting the cavity and jamming mechanical components in the inhaler or creating a rattling noise which would be undesirable for the user.

Although the inhaler may suitably be a single dose inhalation device, the present inventive ideas may also be implemented in a multiple dose inhalation device. Thus, according to at least one example embodiment, the base has a plurality of consecutive sealed cavities containing medicament, each cavity being sealed by a respective associated foil portion, wherein each foil portion is on its other side attached to a separating element associated with a respective cavity for separating a foil portion from that cavity.

For explanatory purposes only, in the following description, it is assumed that the is inhaler is oriented in such way that the cavities are located below the foil portions and that the separating elements are located above the foil portions. Thus, any directional or orientational expressions such as "upper", "lateral", "above", "below" are used herein with said orientation of the inhaler in mind. However, it is to be understood that this definition is only used for creating a simple discussion reference and thus the inhaler according to the invention is not limited to a specific orientation. For simplicity and unnecessary repetition, the following discussion will mainly focus on a multiple dose inhalation device. However, it is to be understood that at least some of the discussed features are applicable also to a single dose inhalation device.

According to at least an embodiment of the invention it is dislosed an inhaler comprising a base having a plurality of medicament-containing sealed cavities which are consecutively movable to a dispensing position of the inhaler, foil portions which on one side are attached to the base for sealing the medicament within respective associated cavities and which on an opposite side are attached to a plurality of separating elements, each separating element being associated with a respective cavity for separating a foil portion from that cavity, an actuator adapted to provide an impact on the separating element associated with the cavity currently located in the dispensing position, thereby moving that separating element to a removed position in which the separating element is moved-away from the cavity so that the sealing foil portion is separated from the cavity which is thereby uncovered so that medicament contained therein is enabled to become entrained in a fluid flow, wherein the cavities are adapted to be indexed relative to the actuator. For a multiple dose inhalation device, it has been realised that the separating element may be used to define different flow paths related to different cavities. Accordingly, rather than obstructing the flow path during subsequent inhalations, the separating element may actually be used to, at least partly, define the different flow paths. Thus, according to at least one example embodiment, each separating element comprises a first wall portion to which the foil portion is attached for, at least partly, defining a flow path for its associated cavity and a second wall portion for, at least partly, defining the flow path for a neighbouring cavity. Thus, it should be understood that this example embodiment may be used in connection with an inhaler comprising a plurality of cavities having individual flow paths. Once the separating element has been removed from the base for allowing an inhalation to take place, it will not obstruct a subsequent inhalation, because the next cavity has its own flow path. Thus, rather than becoming obstructing after its first use, it contributes in a second use in defining another flow path for another cavity.

Although said first and second wall portions of the separating element may be on one and the same side (e.g. due to possible rotation of the separating element), said first and second wall portions are suitably located on different sides of the separating element. This is suitable for creating individual flow paths for the cavities. Thus, by avoiding using the same wall portion twice, the risk of powder remains that have adhered to such a wall portion becoming entrained in a subsequent inhalation flow is considerably reduced. Typically, the first wall portion would face its associated cavity which is located below said first wall portion, thereby being capable of forming an upper flow path-defining wall portion to said associated cavity when lifted from the cavity. Typically, the second wall portion would be at least somewhat perpendicular to said first wall portion, thereby being capable of forming a lateral flow path-defining wall portion to the neighbouring cavity.

When the separating element is distanced from its associated cavity in order to remove the foil and to uncover said cavity, the foil remains attached to the separating element. Thus, the removed foil portion becomes part of the first wall portion for defining the flow path.

The foil portions may be provided as one foil and, optionally, the foil portions may be defined by perforations or other material weakenings. As an alternative to a single foil, the foil portions may be applied in the form of individual patches. The foil portions may be attached to the base and the separating elements by welding, gluing or other suitable method. It should be noted that the terms "foil" and "foil portion" are not limited to a single material layer. On the contrary a foil or foil portion may comprise a plurality of layers. For instance, foil may comprise a metal layer which is coated with lacquer or polymer layer on one or both sides in any suitable combination in order to provide the desired stiffness, attachment capability, etc.

According to at least one example embodiment of the invention, each separating element comprises a third wall portion for, at least partly, defining the flow path for another neighbouring cavity on the other side of said associated cavity. Typically, that third wall portion would be at least somewhat perpendicular to said first wall portion, thereby being capable of forming a lateral flow path-defining wall portion to said other neighbouring cavity.

As previously mentioned, although it is conceivable that the separating elements may be moved in such way that a wall portion performs a flow path-defining function for more than one cavity, it is appropriate that for each one of said wall portions, its flow path-defining function is performed only in relation to one respective cavity. Thus, for instance the first wall portion of a given separating element could partly define a flow path for powder in the cavity below the separating element, while the second and third wall portions could partly define flow paths for the two neighbouring cavities located left and right, respectively, of the separating element.

As mentioned previously, the separating element may be moved away from its associated cavity in order to separate a respective foil portion from said cavity and to create an upper flow path-defining wall portion. Separating elements which are located adjacent to said moved-away separating element may also form part in defining the flow path, typically as lateral flow path-defining wall portions. This is reflected in at least one example embodiment of the invention, wherein said fluid flow is guided by a flow path which is at least partly defined by first, second and third consecutive separating elements, wherein only the intermediate second separating element is in said removed position. In other words each separating element has a first position in which it covers the opening of its associated cavity and a second position (above referred to as "removed position") in which it is distanced from the cavity and allows a fluid flow to entrain medicament from the cavity. Thus, the first position is both the initial position (i.e. the state in which the foil is still attached before removal of the separating element) and the returned position mentioned above (i.e. after the separating element has been removed for bringing along the foil portion and then returned).

It should be noted that the separating elements may return from the second (removed) position to the first (returned) position, in order to function as a lateral flow path-defining is wall portion for a neighbouring cavity. To give an example, assume there are three consecutive cavities: a first cavity having an associated first separating element, a second cavity having an associated second separating element and a third cavity having an associated third separating element. The second separating element could then initially function as a lateral flow path-defining wall portion for a fluid flow that entrains powder from the first cavity (when uncovered). Then, the second separating element can be moved away from the associated second cavity in order to function as an upper flow path-defining wall portion for a fluid flow that entrains powder from the thus uncovered second cavity. Finally, the second separating element can be moved back to the associated second cavity in order to function as a lateral flow path-defining wall portion for a fluid flow that entrains powder from the third cavity (when uncovered).

The above exemplified multiple functionality of the separating element is at least partly reflected in at least one example embodiment of the invention, wherein each separating element has a first (initial or returned) position in which it covers the opening of its associated cavity, and a second (removed) position in which it is distanced from the cavity, wherein each one of said separating elements is in said second (removed) position adapted to at least partly define a flow path for a fluid flow to entrain medicament from the associated cavity, and in said first (initial or returned) position, together with a neighbouring separating element in said second position, adapted to at least partly define a flow path for a fluid flow to entrain medicament from the cavity associated with said neighbouring separating element.

Although, it has been described above that a separating element may, at least partly, form a lateral flow path-defining wall portion for a neighbouring cavity, an alternative would be to provide fixed lateral flow path-defining elements. According to at least one example embodiment of the invention, a partition wall is provided between each pair of neighbouring separating elements, and extends perpendicularly upwards from the base. There would be two lateral partition walls assisting in defining a flow path, one on each lateral side of the cavity (regarded in the fluid flow direction), while the separating element associated with that cavity would, when raised, form an upper flow path-defining wall portion. When assembled, the partition walls could be mounted onto the foil that covers (or is intended to later cover) the cavities in such way that they cause a weakening in the foil, thereby establishing defined foil portions between the partition walls.

According to at least one example embodiment of the invention, each separating element comprises an actuator-receiving portion, wherein the inhaler comprises an actuator adapted to provide a force onto the actuator-receiving portion to cause the separating elements to move from said first position to said second position. The opening force may come from below and push the actuator-receiving portion upwards. Alternatively, the opening force may be achieved by providing an upper pulling force onto the actuator-receiving portion. Thus, depending on the direction of force and the actuator providing the force, the actuator-receiving portion may be designed in various ways, such as protrusions, dogs, hooks, indentations, overhangs, channels, etc.

In order to separate a foil portion from the cavity it is sealing, the foil portion should be appropriately attached to its associated separating element. According to at least one example embodiment of the invention, the attachment force between the separating elements and the respective associated foil portions is larger than the attachment force between the base and the foil portions, whereby movement of such a separating element away from its associated cavity causes the associated foil portion to become separated from the base.

Suitably, the contact area between a foil portion and its associated attached separating element is dimensioned in such way that no flow ruptured obstructing foil parts will remain after the separation has occurred. In other words, the flow path downstream and upstream of the cavity opening should be free from any obstructing fringes of foil. Suitably, on the base, the flow path upstream and downstream of the cavity opening is completely foil free after the separation has occurred. This may be accomplished by designing the separating element with longer (or equal) extension in the flow path direction than that of the foil portion. Since the foil portion extends across the cavity opening in order to seal the cavity, the attached separating element should also extend at least across the cavity opening. As mentioned previously, the foil portions may form part of one covering foil provided with perforations or weakenings which define the foil portions. Such perforations would be present between the cavity openings, and when the foil portions are ruptured at those perforations or weakenings any fringes would be located laterally of the cavity viewed from a flow direction perspective, and consequently no obstructing fringes would be present upstream or downstream of the cavity.

There are various way to obtain a larger attachment force at the separating element/foil portion interface than at the foil portion/base interface. According to at least one example embodiment of the invention, the contact surface between a separating element and its associated foil portion is larger than the contact surface between that foil portion and the base. In other words the separating element/foil portion interface is larger than the foil portion/base interface. If the separating element covers the entire foil portion, then the contact surface will automatically be larger between the separating element and the foil portion than the contact surface between the foil portion and the base, because the piece of the foil portion located directly above the cavity opening is not attached to anything and only the surrounding area of the foil is attached to the base.

Another way to obtain different attachment forces is considered in at least one other example embodiment of the invention. The foil portions may comprise a first coating layer to which the base is attached and a second coating layer to which the separating elements are attached, wherein the tensile strength of the second coating layer is larger than the tensile strength of the first coating layer. The layers can provide different bonding properties, e.g. welds of different types of material, or glues of different types or amounts, or any combination thereof.

Other ways to obtain the difference in attachment forces could be to provide the separating element with specially designed geometric features, e.g. grooves into which the foil may be attached or other features that e.g. pierce the foil to create a firm grip.

Although the foil portion may be folded into grooves of the separating element or otherwise curved around the separating element e.g. to increase the attachment area, the foil portion may suitably just be flat, i.e. only extending in a single plane parallel to the base. This enables a simple assembling of the separating elements to the foil portions. When they have become assembled the foil may be attached to the base. An alternative would be to first attach the foil portions to the base, and then attach the separating elements onto the respective foil portions.

Suitably, the stiffness of the separating elements is substantially larger than the stiffness of the foil portions, wherein the separating elements enable the foil portions to perform a rigid body motion, and may thus become snapped off the base rather than peeled off.

Although the above exemplified embodiments have discussed one cavity having one associated separating element, an alternative would be to have two cavities having one common associated separating element. For instance, if two incompatible drug components are to be inhaled essentially simultaneously, they are suitably be provided in two separate cavities. The two cavities may be covered and sealed by one common foil portion (or one foil portion each), which in turn is attached to a common associated separating element extending across both cavities. Thus, when the separating element is moved away from the cavity, it will bring along the foil portion, uncovering both cavities from which the drug components can be entrained in an inhalation flow. The cavities could either be located in series in the base, i.e. one cavity being downstream of the other one, or they could be located in parallel, i.e. the inhalation flow reaches the cavities essentially simultaneously.

Although an inhaler may be linear having the consecutive cavities aligned along a straight line, it may suitably be designed as a generally annular shape. In particular, according to at least one example embodiment of the invention, the base is shaped as a circular disk and the cavities are provided consecutively in a circular arrangement or path around the disk. Thus, when medicament has been inhaled from one cavity, the base is rotated relative to a mouthpiece or nasal adaptor of the inhaler in order to index the inhaler to the next cavity.

According to at least a second aspect of the invention, there is provided a method in an inhaler comprising a base having a plurality of medicament-containing cavities which may consecutively be moved to a dispensing position of the inhaler, the inhaler being provided with foil portions which on one side are attached to the base for sealing the medicament within respective associated cavities and which on an opposite side are attached to a plurality of separating elements, each separating element being associated with a respective cavity for separating a foil portion from that cavity. The method comprises:

moving a separating element away from its associated cavity so that the sealing foil portion becomes separated from the cavity which becomes uncovered, entraining in a fluid flow medicament from the uncovered cavity when said uncovered cavity is in said dispensing position, returning the moved separating element to cover its associated cavity, indexing the base to move the next cavity to said dispensing position.

The separation of the foil portion from the cavity by moving away of the separating element may, for instance, be performed before said indexing. Another alternative would be to perform the separation after said indexing. The above method may be used in inhalers as discussed in connection with the first aspect of the invention, i.e. the inhalers having separating elements which act as flow path-defining elements both for respective associated cavities and for neighbouring cavities. The above method may, however, also be used in inhalers in which each separating element only act as a flow path-defining element for its associated cavity which it has covered. For instance, partition walls may be provided between the separating elements and extend perpendicularly upwards from the base. Such partition walls would form lateral flow path-defining wall portions, while a raised separating element would form the upper flow path-defining wall portion. When assembled, the partition walls could be mounted onto the foil covering (or intended to later cover) the cavities in such way that they cause a weakening in the foil, thereby establishing defined foil portions between the partition walls.

According to at least one example embodiment of the invention, said act of moving comprises applying a force which pushes the separating element away from the cavity. An alternative is that said act of moving comprises applying a force which pulls the separating element away from the cavity.

According to at least one example embodiment of the invention, the method comprises, after said moving away of the separating element, aligning it such that a side of the separating element facing the cavity opening becomes located in parallel with the cavity opening. Thus, referring to the terminology used when discussing the first aspect of the invention, the first wall portion would be aligned in parallel with and facing its associated cavity which is located below said first wall portion, thereby being capable of forming an upper flow path-defining wall portion to said associated cavity when lifted from the cavity, said upper flow path-defining wall portion being parallel with the plane defined by the rim of the cavity opening. This allows of a fluid flow which may travel essentially in parallel with the plane defined by the rim of the cavity opening, wherein such fluid flow does not per se enter the cavity but instead creates an eddy or a vortex in the cavity which causes the medicament to leave the cavity and join the fluid flow. Depending on the desired flow path characteristics, there are other alternatives to having such parallel alignment of the separating element and the cavity opening. For instance, it would be conceivable to provide the facing side of the moved separating element at an inclination angle (other than a zero angle, which would be the parallel alignment) against the plane defined by the rim of the cavity opening. This allows of a fluid flow to be directed at least partly into the cavity, or to increase or decrease the flow velocity, or other possible effects.

It should be understood that the second aspect of the invention encompasses any embodiments or any features described in connection with the first aspect of the invention, as long as those embodiments or features are compatible with the method of the second aspect.

The inhaler may contain various drugs and/or bioactive agents to be inhaled.

The bioactive agent may be selected from any therapeutic or diagnostic agent. For example it may be from the group of antiallergics, bronchodilators, bronchoconsitrictors, pulmonary lung surfactants, analgesics, antibiotics, leukotrine inhibitors or antagonists, anticholinergics, mast cell inhibitors, antihistamines, antiinflammatories, antineoplastics, anaesthetics, anti-tuberculars, imaging agents, cardiovascular agents, enzymes, steroids, genetic material, viral vectors, antisense agents, proteins, peptides and combinations thereof.

Examples of specific drugs which can be incorporated in the inhalation device according to the invention include mometasone, ipratropium bromide, tiotropium and salts thereof, salemeterol, fluticasone propionate, beclomethasone dipropionate, reproterol, clenbuterol, rofleponide and salts, nedocromil, sodium cromoglycate, flunisolide, budesonide, formoterol fumarate dihydrate, Symbicort™ (budesonide and formoterol), terbutaline, terbutaline sulphate, salbutamol base and sulphate, fenoterol, 3-[2-(4-Hydroxy-2-oxo-3H-1,3-benzothiazol-7-yl) ethylamino]-N-[2-(4-methylphenyl) ethoxy]ethyl]propanesulphonamide, hydrochloride. All of the above compounds can be in free base form or as pharmaceutically acceptable salts as known in the art.

Combinations of drugs may also be employed, for example formoterol/budesonide; formoterol/fluticasone; formoterol/mometasone; salmeterol/fluticasone; formoterol/tiotropium salts; zafirlukast/formoterol, zafirlukast/budesonide; montelukast/formoterol; montelukast/budesonide; loratadine/montelukast and loratadine/zafirlukast.

Further combinations include tiotropium and fluticasone, tiotropium and budesonide, tiotropium and mometasone, mometasone and salmeterol, formoterol and rofleponide, salmeterol and budesonide, salmeterol and rofleponide, and tiotropium and rofleponide.

BRIEF DESCRIPTION OF THE DRAWINGS

FIGS. 4a-4e schematically illustrate an alternative operating sequence which includes separating a foil portion from the cavity that it is covering and dispensing the medicament contained in the cavity.

FIG. 6 schematically illustrates an example embodiment as an alternative to what is illustrated in FIG. 5a.

DETAILED DESCRIPTION OF THE DRAWINGS

Figure 1:
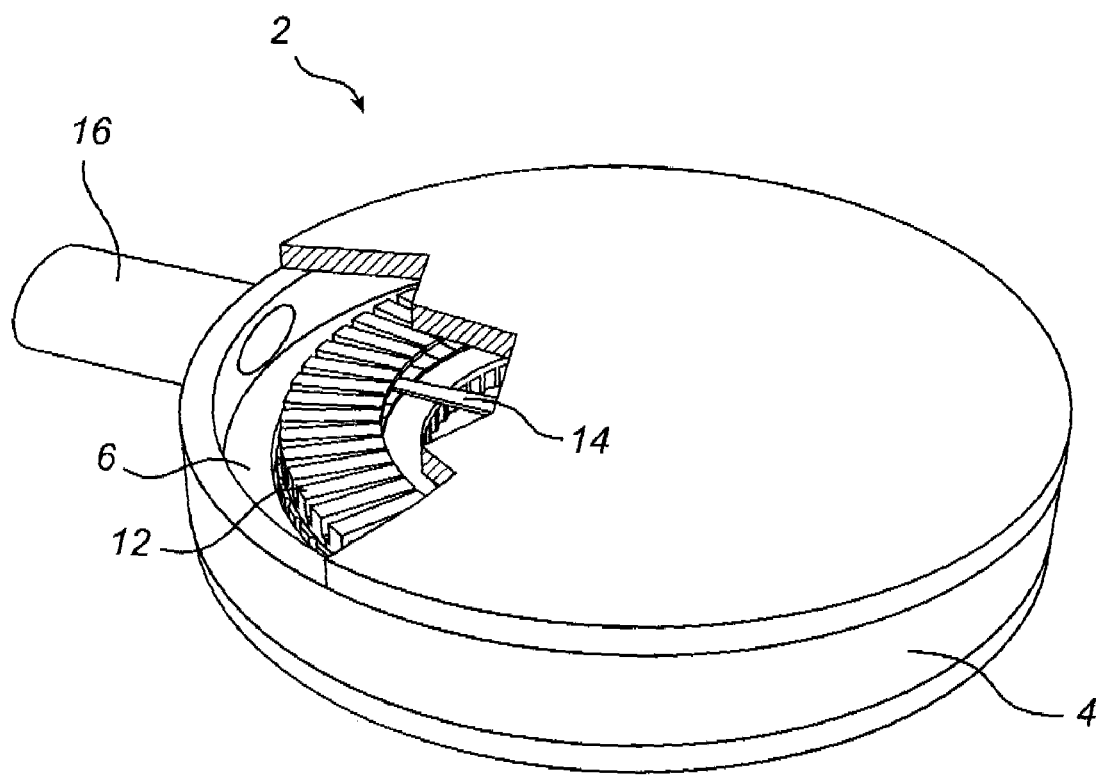
FIG. 1 is a schematic view of an inhaler according to at least one example embodiment of the invention, part of the inhaler housing being cut-away to illustrate some internal details.

FIG. 1 is a schematic view of an inhaler 2, part of the inhaler housing 4 being cut-away to illustrate some internal details. The housing 4 encloses a base 6 having a plurality of cavities 8 sealed by a foil 10 (see FIG. 2). For each cavity 8, there is attached a separating element 12 on top of the foil. An actuator 14, herein illustrated as comprising an arm, extends from a central location of the inhaler 2. The actuator 14 is adapted to engage one separating element 12 at a time and to move it upwardly in order to separate a foil portion from the cavity 8 below the separating element 12. Thereby, medicament contained in the cavity 8 can be entrained in a fluid flow to be inhaled by a user. In this example, the fluid flow is in the form of an air-flow and the medicament exits the inhaler 2 via a mouthpiece 16.

The actuator 14 may be manually operated by pushing, pressing, rotating etc. a button, lever or the like on the inhaler housing 4 (not shown), or may be triggered by a user's inhalation in which case it would be latched by an air-flow sensitive release mechanism (not shown).

Before, during or after inhalation the base 6 is rotated (indexed) to bring the next cavity 8 into position. This may be implemented in various ways, such as using a standard lever on the housing 4. Another alternative could be to use a connection between the base 6 and a mouthpiece cover, wherein removal (or replacement) of the mouthpiece cover would cause the base 6 to index one step to the next cavity 8. Yet another alternative could be to use a breath-triggering mechanism to cause the base 6 to index one step.

The inhaler 2 may suitably comprise a structure that provides a moisture protection, such as e.g. a moisture absorbent sink as described in WO2006/000758, or any other appropriate alternative for including desiccant material.

Figure 2:
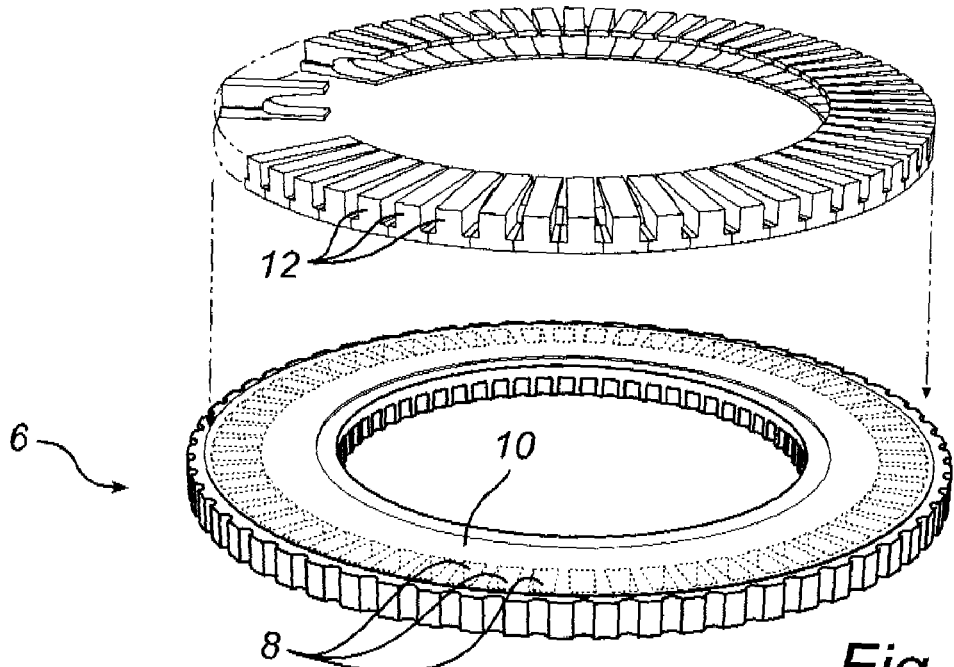
FIG. 2 illustrates schematically the assembling of separating elements onto a base having a plurality of cavities.

FIG. 2 illustrates schematically the assembling of separating elements 12 onto a base 6 is having a plurality of cavities 8. The base 6 has a general annular and circular shape, wherein the cavities 8 are arranged in a circular path along the base. When the cavities have been provided with powdered medicament, a foil 10 may be placed on the base 6 to seal the cavities 8, and then a plurality of separating elements 12 are placed on top of the foil 10 so as to mate and align each separating element 12 with a respective cavity 8. Alternatively, the plurality of separating elements 12 may first be attached to a foil and then said foil is attached to the base 6 to seal the cavities 8. Whichever alternative is used, the foil 10 may be provided with perforations or weakenings to define foil portions that are readily separable from the cavities when the separating element is lifted from the base. Such perforations or weakenings may e.g. be performed in a separate production step, but could alternatively be achieved when the foil is attached to the base and/or the separating elements if the base and/or the separating elements have structural features which create the perforations or weakenings during the attachment step. The finished assembly of base 6, foil 10 and separating elements 12 may then inserted into the housing 4 or some other holding structure, e.g. as disclosed in WO2006/000758.

Most components of the inhaler 2, such as the base 6, the separating elements 12 and the actuator 14 are suitably made of a plastic material, such as a polymer, however, other materials, such as metal or ceramic are conceivable alternatives.

FIGS. 3a-3e schematically illustrate an operating sequence which includes separating a foil portion 110 from the cavity 108 that it is covering and dispensing the medicament contained in the cavity 108.

Figure 3A:
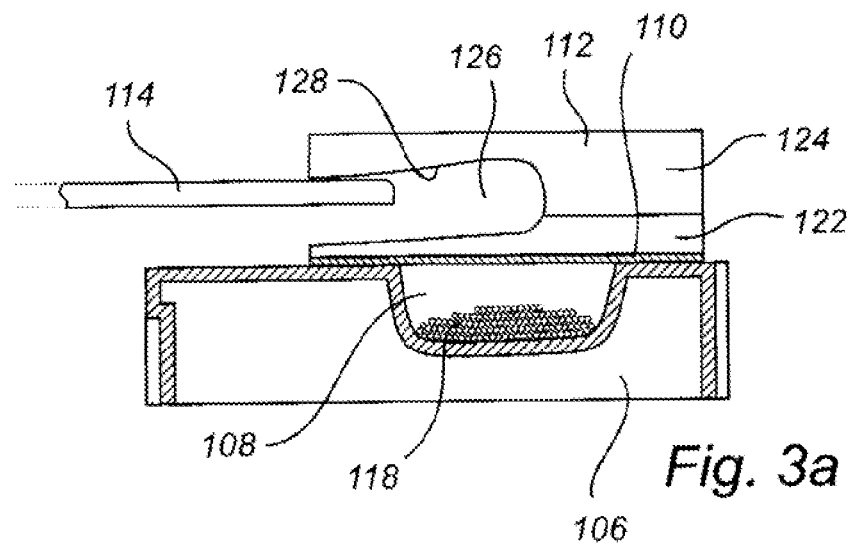
FIGS. 3a-3e schematically illustrate an operating sequence which includes separating a foil portion from the cavity that it is covering and dispensing the medicament contained in the cavity.

FIG. 3a is a cross-sectional view of a cavity 108 in the base 106, wherein the cavity 108 contains powdered medicament 118 and is sealed by a foil portion 110. The foil portion 110 is attached by any suitable type of bonding, welding, gluing etc, to an area of the base 106 which surrounds the rim of the cavity opening. A separating element 112 is attached by any suitable type of bonding, welding, gluing, etc. to the foil portion 110. In the extension of the flow path direction, the separating element 112 covers the entire foil portion 110, the flow path direction being illustrated by the arrows in FIG. 3d. Thus, the contact area between the separating element 112 and the foil portion 110 is larger than the contact area between the foil portion 110 and the base 106, enabling the achievement of a larger attachment force between the separating element 112 and the foil portion 110 compared to the attachment force between the foil portion 110 and the base 106.

The separating element 112 comprises a lower portion 122 and an upper portion 124, which may be produced in one piece or as two separate pieces joined together. There is a space 126 between the lower portion 122 and the upper portion 124. The space 126 is formed like a bay which opens towards the centre of the inhaler, i.e. towards the actuator 114. The upper portion 124 has an underside 128 that faces the space 126 and the lower portion 122, said underside 124 being somewhat curved to enable the actuator 114 to tilt and align the separating element 112 as will be explained in relation to FIGS. 3b-3c. In the position illustrated in FIG. 3a, the actuator 114 has been inserted substantially horizontally into the space 126.

Figure 3B:
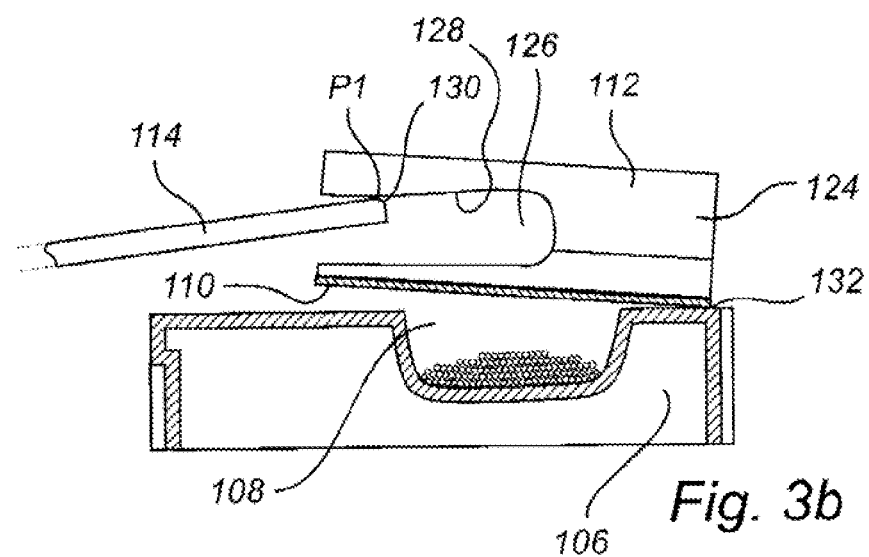

As the end portion 130 of the actuator 114 is pivoted upwards to a certain inclination, it engages the underside 128 of the upper portion 124 at a first point P1, affecting it with a lifting force, as illustrated in FIG. 3b. This causes the separating element 112 together with the attached seal or foil portion 110 to be raised in a pivoting motion, around a pivot point 132 at the end of the foil/base interface downstream of the cavity 108.

Figure 3C:
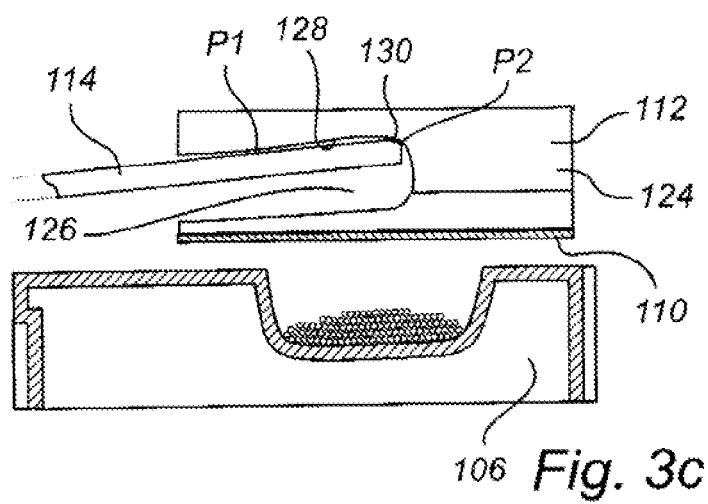

The actuator 114, with maintained angle of inclination, then moves forward in the flow direction, i.e. further into the bay-shaped space 126. This causes the foil portion 110 and the attached separating element 112 to completely separate from the base 106. Further into the bay-shaped space 126, the underside 128 is more cut out than at said first point P1 of the underside 128. When the end portion 130 of the actuator 114 reaches an inner second point P2 of the underside 128, the separating element 112 has been pivoted in the other direction, bringing the separated foil portion 110 into a plane which is parallel with the main plane of the base 106, as illustrated in FIG. 3c. This is due to the curvature of the underside of the upper portion 124. The vertical distance (vertical in this case being e.g. the direction from the base 106 towards the separating element 112) between said first point P1 and said second point P2 is dimensioned to be equal to the vertical distance between those portions of the actuator 114 that contact said first and second points, respectively, when the actuator 114 is at a desired angle of inclination. It should be understood, that this is just an example embodiment, and that it would be conceivable to use another curvature of the underside in order to obtain another orientation of the separating element and the attached foil portion in relation to the base.

Figure 3D:
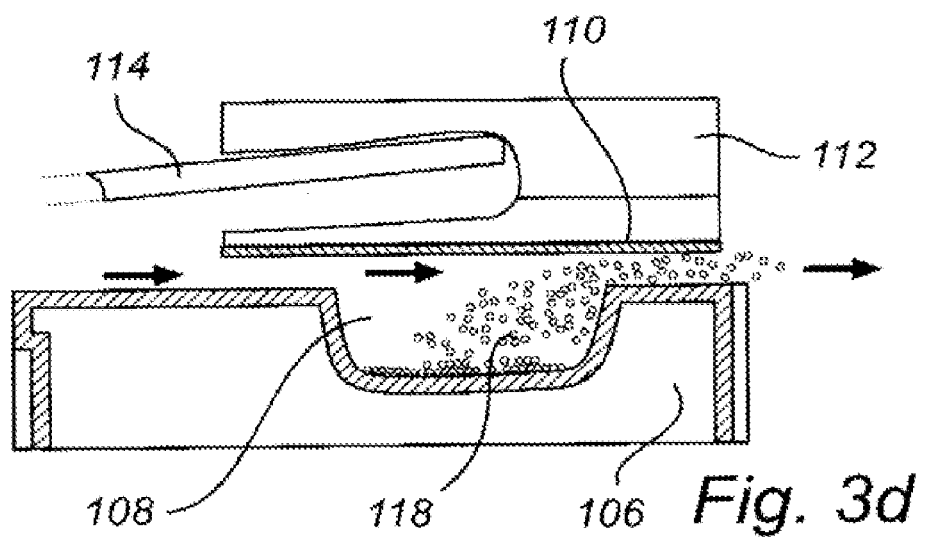
Figure 3E:
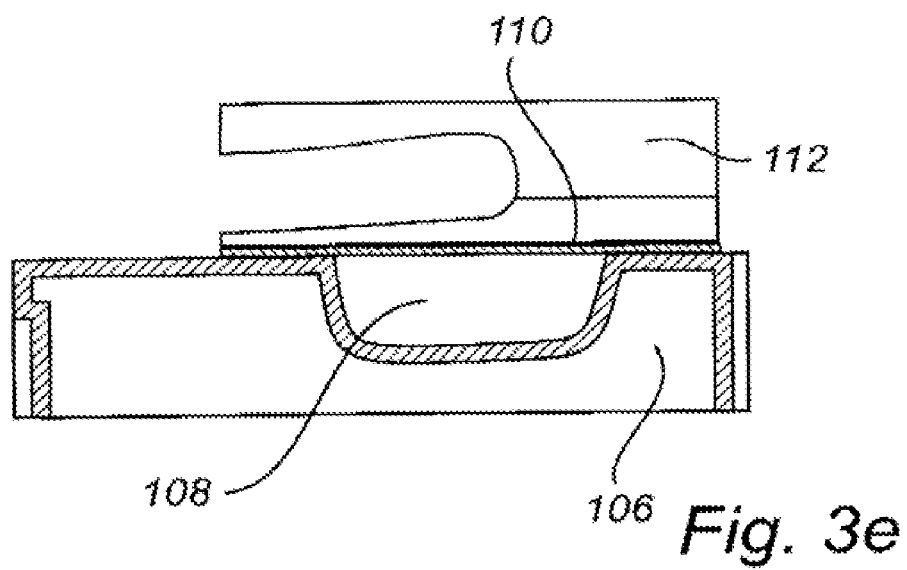
Figure 5A:
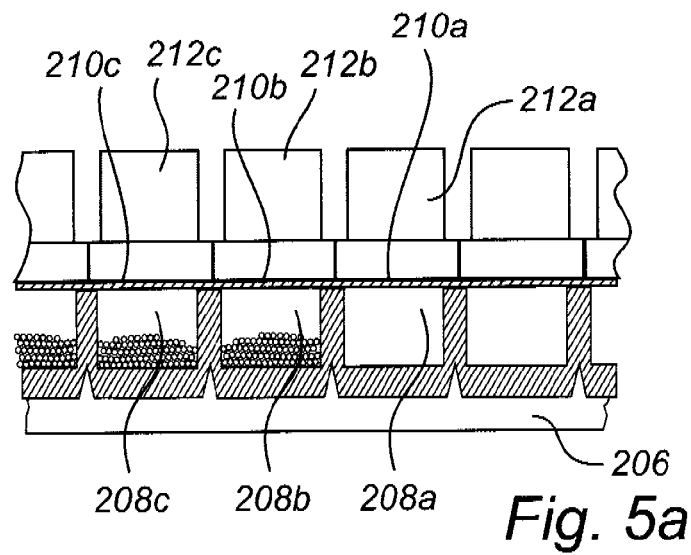
FIGS. 5a-5c schematically illustrate a sequence which substantially corresponds to the sequence illustrated in FIGS. 3a-3c, however viewed against the direction of the fluid flow.

As illustrated in FIG. 3*d*, when the foil portion 110 has been completely separated from the base 106 and the cavity 108 and reached a desired position, the fluid flow may entrain the powdered medicament 118 from the cavity 108. The direction of the fluid flow is illustrated by the arrows, upstream being towards the centre of the inhaler 2 with respect to the cavity 108 and downstream being radially towards the mouthpiece 16 (see FIG. 1). The fluid flow, may be initiated in response to a user inhaling through the mouthpiece 16. Alternatively, it may be actuated by manually releasing a built-up pressure in a pressure chamber which is in communication with the flow path extending between the raised separating element 112 (including foil portion 110) and the base 106.

After inhalation, the actuator 114 is removed and the separating element 112 with the attached foil portion 110 becomes lowered onto the base 106 to a returned position, which corresponds to its initial position, once again covering the cavity 108, as illustrated in FIG. 3*e*.

Although, in FIGS. 3*a*-3*e*, the actuator 114 has been illustrated as comprising an arm and the separating element 112 has been illustrated as comprising a bay-shaped space 126 between an upper portion 124 and a lower portion 122, other alternative embodiments are conceivable for moving the separating element 112 with the attached foil portion 110 away from the base 106. The illustrated example embodiments are not limiting in any way and are merely included for explanatory purposes.

FIGS. 4*a*-4*e* schematically illustrate an operating sequence which includes separating a foil portion 110 from the cavity 108 that it is covering and dispensing the medicament contained in the cavity 108.

FIG. 4*a* is a cross-sectional view of a cavity 108 in the base 106, wherein the cavity 108 contains powdered medicament and is sealed by a foil portion 110. The foil portion 110 is attached by any suitable type of bonding, welding, gluing etc, to an area of the base 106 which surrounds the rim of the cavity opening. A separating element 112' is attached by any suitable type of bonding, welding, gluing, etc. to the foil portion 110. In the extension of the flow path direction, the separating element 112' covers the entire foil portion 110, the flow path direction being illustrated by the arrows in FIG. 4*d*. Thus, the contact area between the separating element 112' and the foil portion 110 is larger than the contact area between the foil portion 110 and the base 106, enabling the achievement of a larger attachment force between the separating element 112' and the foil portion 110 compared to the attachment force between the foil portion 110 and the base 106.

The separating element 112' comprises a lower portion and an upper portion, which may be produced in one piece or as two separate pieces joined together. There is an upper surface 140 of the separating element 112'. The upper surface 140 describes a sloping path at the part which is situated towards the centre of the inhaler, i.e. towards the actuator 114'. The actuator 114' is a claw adapted to fit around the edge of the separating element 112'. When the claw is pivoted the movement makes it engage with the separating element 112' and to tilt and align the separating element 112 as will be explained in relation to FIGS. 4*b*-4*c*. The actuator 114' comprises an upper end portion 151 and a lower end portion 152.

As the end portion 152 of the actuator 114' is pivoted upwards to a certain inclination, it engages the underside 128 of the separating element 112' at a first point P1, affecting it with a lifting force, as illustrated in FIG. 4*b*. This causes the separating element 112' together with the attached seal or foil portion 110 to be raised in a pivoting motion, around a pivot point at the end of the foil/base interface downstream of the cavity 108.

The actuator 114' then pivots further for engagement of the upper end portion 151 with the sloping path 140. This causes the foil portion 110 and the attached separating element 112' to completely separate from the base 106. When the end portion 151 of the actuator 114' reaches an inner second point P2 of the underside 128, the separating element 112' has been pivoted in the other direction, bringing the separated foil portion 110 into a plane which is parallel with the main plane of the base 106, as illustrated in FIG. 4*c*. This is due to the curvature of the sloping portion of the upper portion 140. The vertical distance (vertical in this case being e.g. the direction from the base 106 towards the separating element 112) between said first point P1 and said second point P2 is dimensioned to be equal to the vertical distance between those portions of the actuator 114' that contact said first and second points, respectively, when the actuator 114' is at a desired angle of inclination. It should be understood, that this is just an example embodiment, and that it would be conceivable to use another curvature of the sloping portion in order to obtain another orientation of the separating element and the attached foil portion in relation to the base.

As illustrated in FIG. 4*d*, when the foil portion 110 has been completely separated from the base 106 and the cavity 108 and reached a desired position, the fluid flow may entrain the powdered medicament 118 from the cavity 108. The direction of the fluid flow is illustrated by the arrows, upstream being towards the centre of the inhaler 2 with respect to the cavity 108 and downstream being radially towards the mouthpiece 16 (see FIG. 1). The fluid flow, may be initiated in response to a user inhaling through the mouthpiece 16. Alternatively, it may be actuated by manually releasing a built-up pressure in a pressure chamber which is in communication with the flow path extending between the raised separating element 112' (including foil portion 110) and the base 106.

After inhalation, the actuator 114' is removed and the separating element 112' with the attached foil portion 110 becomes lowered onto the base 106 to a returned position, which corresponds to its initial position, once again covering the cavity 108, as illustrated in FIG. 4*e*.

Although, in FIGS. 4*a*-4*e*, the actuator 114' has been illustrated as comprising a claw and the separating element 112' has been illustrated as comprising a sloping portion 140 at an upper portion positioned towards the centre of the inhaler, other alternative embodiments are conceivable for moving the separating element 112' with the attached foil portion 110 away from the base 106. The illustrated example embodiments are not limiting in any way and are merely included for explanatory purposes.

FIGS. 5*a*-5*c* schematically illustrate a sequence which substantially corresponds to the sequence illustrated in FIGS. 3*a*-3*c*, however viewed against the direction of the fluid flow. For facilitating the understanding of the following discussion, there will be referred to a first cavity 208*a*, a second cavity 208*b* and a third cavity 208*c*. They are covered by is respective first, second and third foil portions 210*a*-210*c* and respective first, second and third separating elements 212*a*-212*c*.

Medicament powder in the first cavity 208a has already been entrained in a fluid flow after the associated separating element 212a has removed the covering foil portion 210a from the cavity 208a. As illustrated in FIG. 5a, the separating element 212a with the attached foil portion 210a has been returned to the base 206 to cover the first cavity 208a. The second cavity 208b is still sealed by a foil portion 210b and is next to be presented for inhalation of medicament. The third cavity 208c will be presented in position for inhalation after the medicament has been dispensed from the second cavity 208b.

Figure 5B:
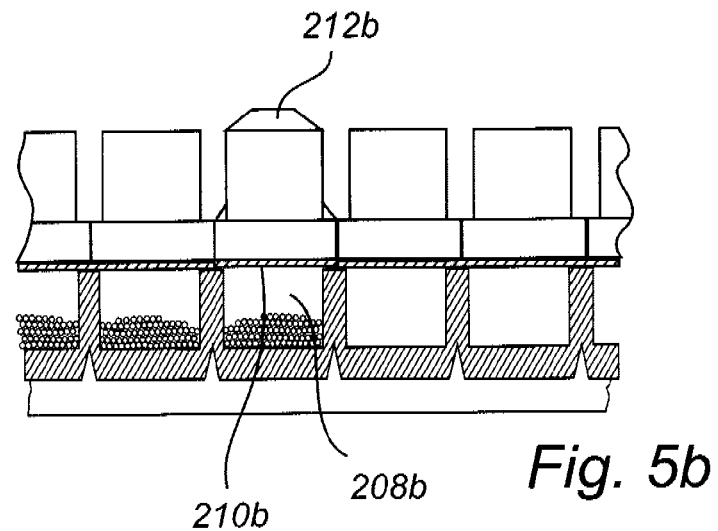

FIG. 5b illustrates the upwards pivoting of the second separating element 212b and attached foil portion 210b which are covering the second cavity 208b, thus corresponding to the action illustrated in FIG. 3b.

Figure 5C:
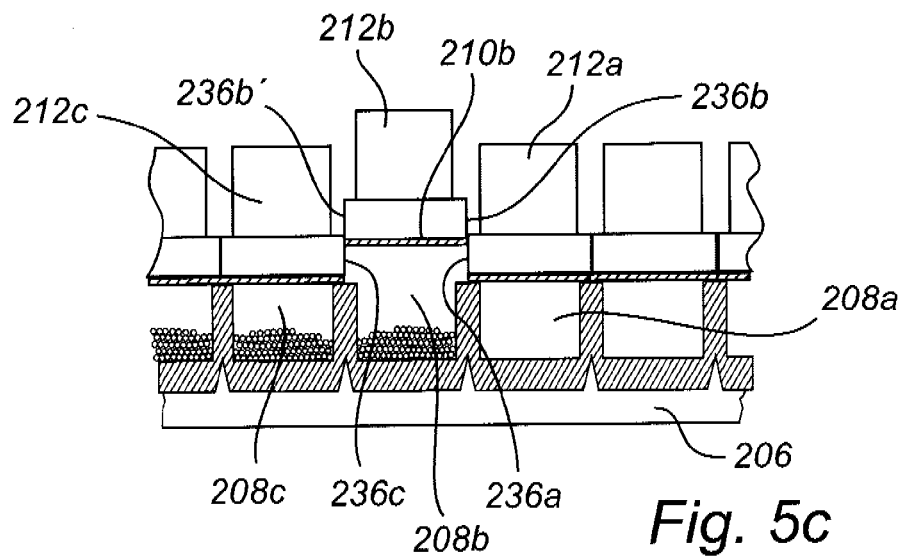

FIG. 5c illustrates the second cavity 208b being completely uncovered as the separating element 212b has completely removed the foil portion 210b from the base 206 and the second cavity 208b, thus corresponding to the position illustrated in FIG. 3c. In this position, the powdered medicament may become entrained in a fluid flow by-passing or entering the second cavity 208b. The flow path is upwardly defined by the second foil portion 210b attached to the second separating element 212b, and is thus now considered as part of the second separating element 212b. The underside of this separating element 212b and the attached foil portion 210b thus form a first flow path-defining wall portion. The first separating element 212a and the third separating element 212c have a lateral flow path-defining wall portion 236a, 236c each for the same flow path.

It should thus be noted, that different wall portions of a separating element will be used for defining flow paths for different cavities. One wall portion is used for the associated cavity below the separating element, and other wall portions are used for neighbouring cavities. Thus, the second separating element 212b also has a lateral second wall portion 236b which has already been used for defining a flow path for entraining medicament from the first cavity 208a. Furthermore, the second separating element 212b has a lateral third wall portion 236b' which will be used for defining a flow path when medicament is to be entrained from the third cavity 208c.

Figure 4A:
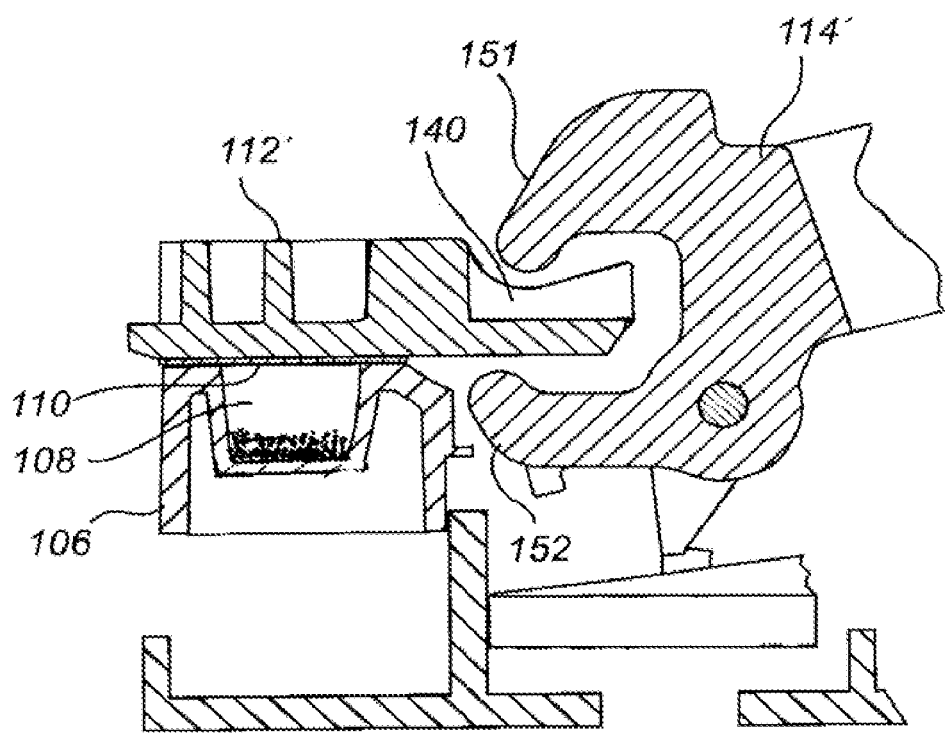
Figure 4B:
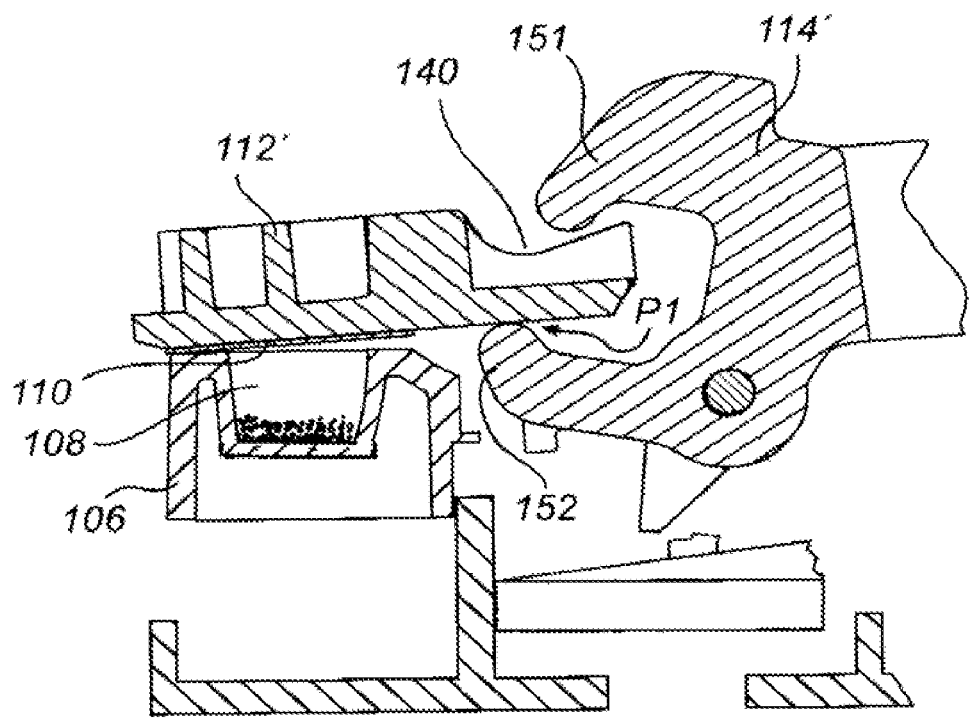
Figure 4D:
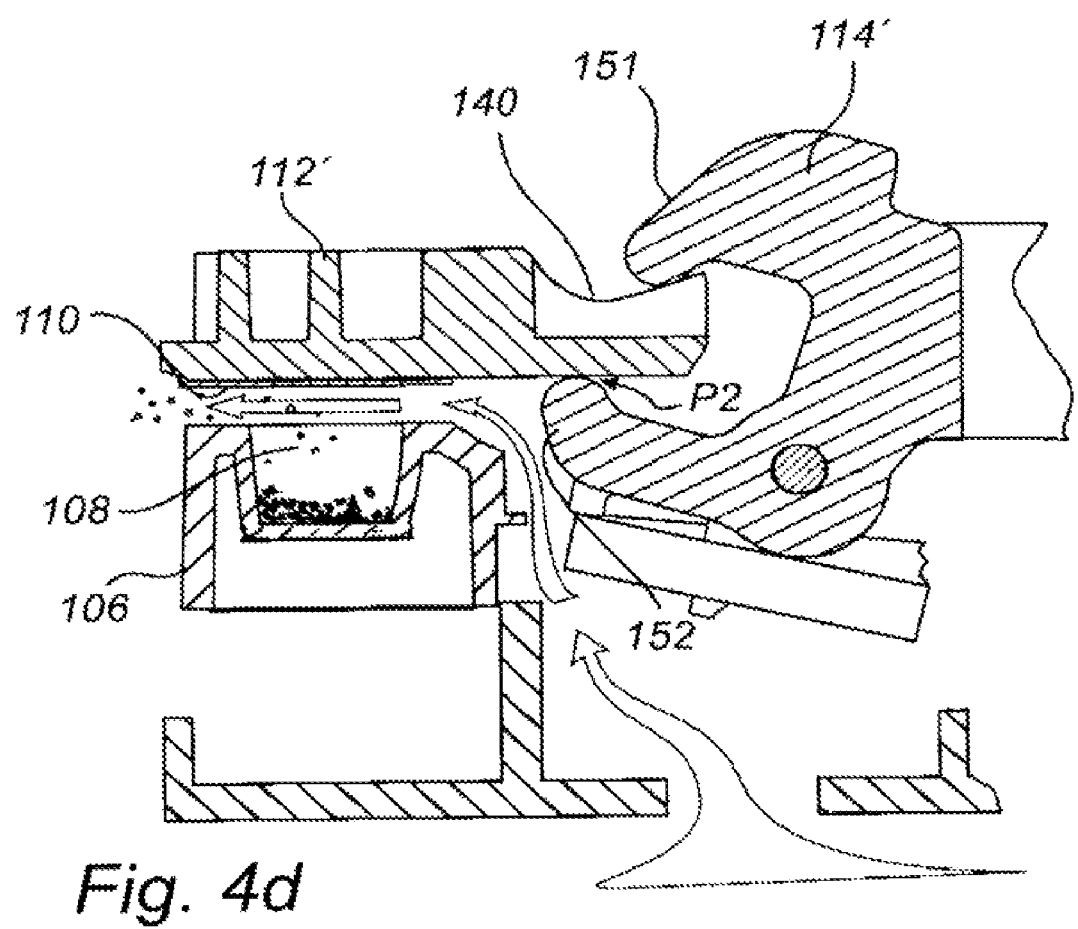
Figure 4E:
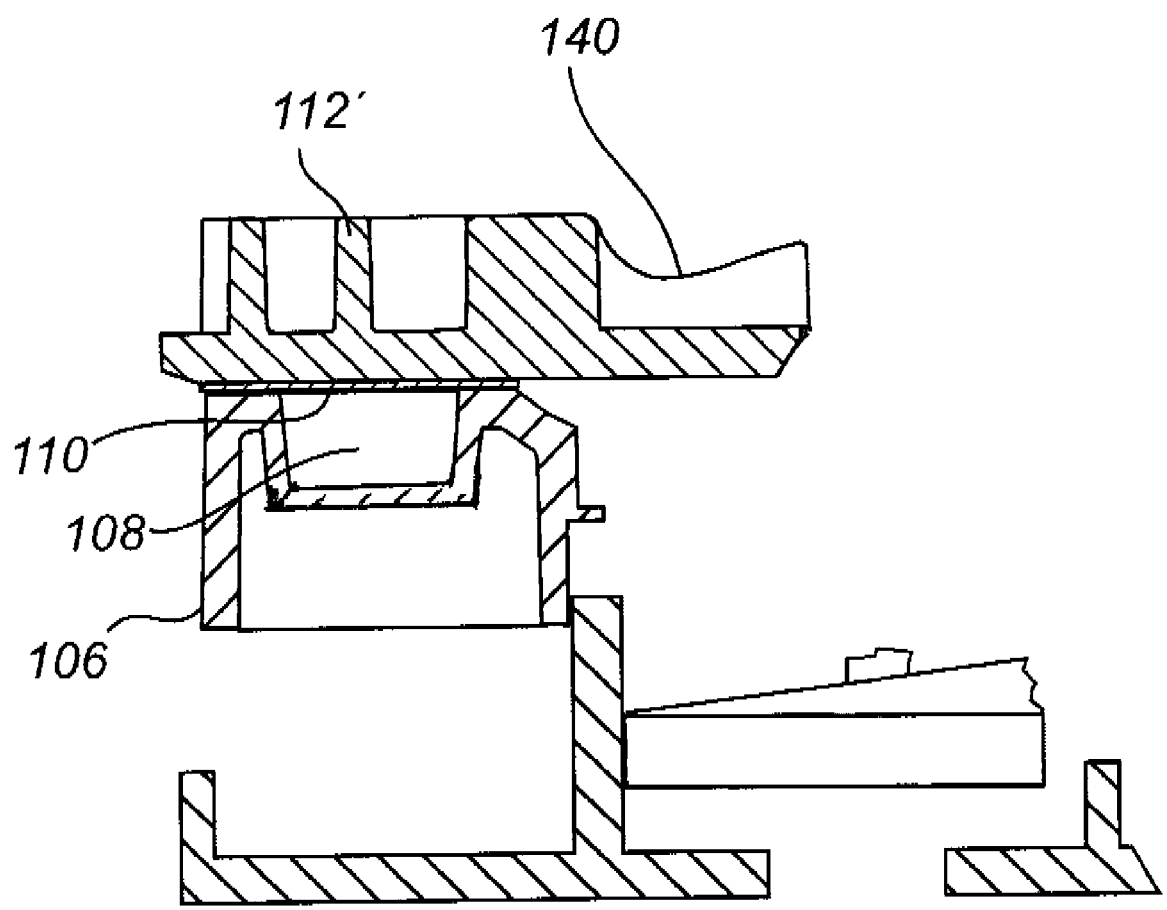
Figure 6:
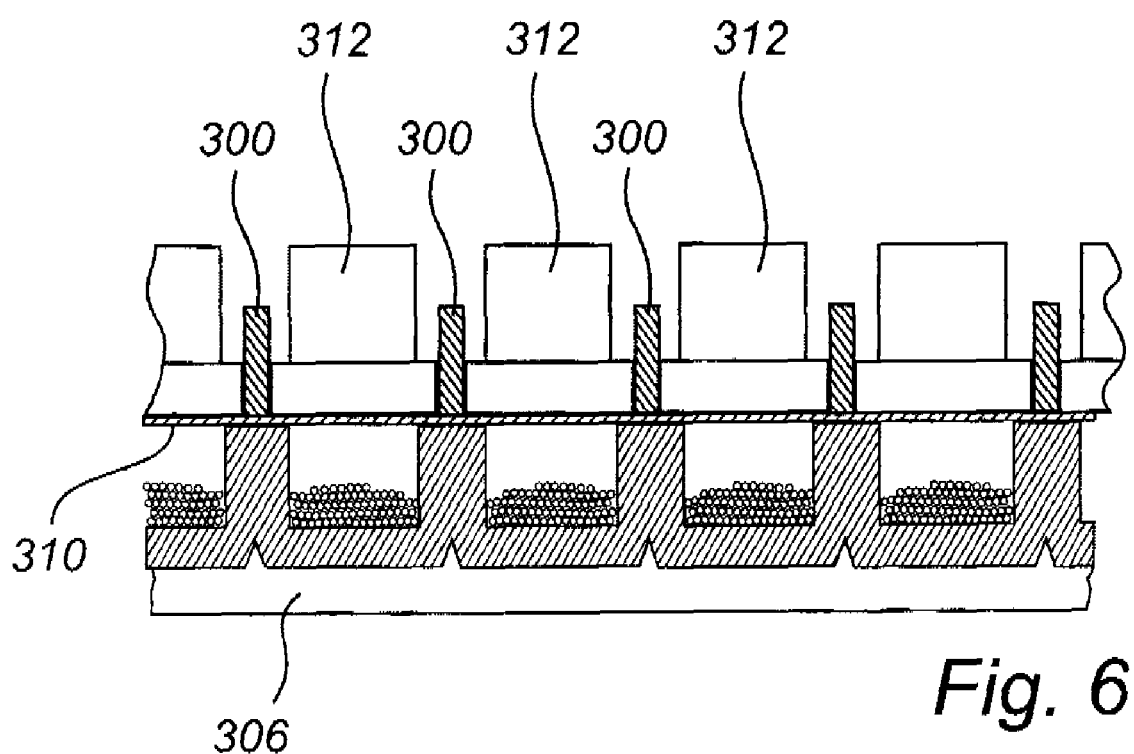

FIG. 6 schematically illustrates an example embodiment as an alternative to what is illustrated in FIG. 4a. Partition walls 300 are provided between neighbouring separating elements 312. The partition walls 300 extends perpendicularly upwards from the foil 310 on the base 306. Thus, when a separating element 312 is moved away from the base 306, there will be two lateral partition walls 300 assisting in defining a flow path, while the moved separating element 312 will form an upper flow path-defining wall portion.

The invention claimed is:

1. An inhaler, comprising
a base having a plurality of medicament-containing sealed cavities which are consecutively movable to a dispensing position of the inhaler,
foil portions which on one side are attached to the base for sealing the medicament within respective associated cavities and which on an opposite side are attached to a plurality of separating elements, each separating element being associated with a respective cavity for separating a foil portion from that cavity, and
an actuator adapted to provide an impact on the separating element associated with the cavity currently located in the dispensing position, thereby moving that separating element to a removed position in which the separating element is moved-away from the cavity so that the sealing foil portion is separated from the cavity which is thereby uncovered so that medicament contained therein is enabled to become entrained in a fluid flow,
wherein, in the removed position of the separating element, the attached foil portion at least partly defines a flow path for the medicament entrained from the cavity and a side of the separating element facing a cavity opening is located in parallel with the cavity opening.

2. An inhaler, comprising
a base having a plurality of medicament-containing sealed cavities which are consecutively movable to a dispensing position of the inhaler,
foil portions which on one side are attached to the base for sealing the medicament within respective associated cavities and which on an opposite side are attached to a plurality of separating elements, each separating element being associated with a respective cavity for separating a foil portion from that cavity, and
an actuator adapted to provide an impact on the separating element associated with the cavity currently located in the dispensing position, thereby moving that separating element to a removed position in which the separating element is moved-away from the cavity so that the sealing foil portion is separated from the cavity which is thereby uncovered so that medicament contained therein is enabled to become entrained in a fluid flow,
wherein the cavities are adapted to be indexed relative to the actuator,
and wherein in the removed position of the separating element a side of the separating element facing a cavity opening is located in parallel with the cavity opening.

3. An inhaler as claimed in claim 2, wherein, in the removed position of the separating element, the attached foil portion at least partly defines a flow path for the medicament entrained from the cavity.

4. The inhaler as claimed in claim 3, wherein the separating element comprises a returned position in which the separating element with the attached foil portion is moved back to cover its associated cavity.

5. The inhaler as claimed in claim 4, wherein a partition wall is provided between each pair of neighbouring separating elements, and extends perpendicularly upwards from the base.

6. The inhaler as claimed in claim 5, wherein the attachment force between each separating element and the respective associated foil portion is larger than the attachment force between the base and the foil portion, whereby movement of the separating element away from its associated cavity causes the associated foil portion to become separated from the base.

7. The inhaler as claimed in claim 6, wherein the contact surface between a separating element and its associated foil portion is larger than the contact surface between that foil portion and the base.

8. The inhaler as claimed in claim 7, wherein each foil portion comprises a first coating layer to which the base is attached and a second coating layer to which the separating element is attached, wherein the tensile strength of the second coating layer is larger than the tensile strength of the first coating layer.

9. The inhaler as claimed in claim 8, wherein the stiffness of each separating element is substantially larger than the stiffness of the associated foil portion, wherein the separating element enables the foil portion to perform a rigid body motion.

10. The inhaler as claimed in claim 9, wherein said base is shaped as a circular disk and wherein the cavities are provided consecutively in a circular arrangement around the disk.

11. A method of operating an inhaler comprising a base having a plurality of medicament-containing cavities which may consecutively be moved to a dispensing position of the inhaler, the inhaler being provided with foil portions which on one side are attached to the base for sealing the medicament within respective associated cavities and which on an opposite side are attached to a plurality of separating elements, each separating element being associated with a respective cavity for separating a foil portion from that cavity, the method comprising:

moving a separating element away from its associated cavity so that the sealing foil portion becomes separated from the cavity which becomes uncovered, entraining in a fluid flow medicament from the uncovered cavity when said uncovered cavity is in said dispensing position, returning the moved separating element to cover its associated cavity, indexing the base to move the next cavity to said dispensing position: and after said moving away of the separating element, aligning it such that a side of the separating element facing the cavity opening becomes located in parallel with the cavity opening.

12. The method as claimed in claim 11, wherein said act of moving comprises applying a force which pushes the separating element away from the cavity.

13. The method as claimed in claim 12, comprising, after said moving away of the separating element, aligning it such that a side of the separating element facing the cavity opening becomes located at a pre-defined angle in relation to the cavity opening.

* * * * *